United States Patent
Aldahwi

(10) Patent No.: US 12,148,520 B1
(45) Date of Patent: Nov. 19, 2024

(54) VIRTUAL THERAPY-BASED APPARATUS AND METHOD FOR TREATMENT OF PSYCHOLOGICAL ISSUES

(71) Applicant: Samara Aldahwi, Los Angeles, CA (US)

(72) Inventor: Samara Aldahwi, Los Angeles, CA (US)

( * ) Notice: Subject to any disclaimer, the term of this patent is extended or adjusted under 35 U.S.C. 154(b) by 0 days.

(21) Appl. No.: 18/600,597

(22) Filed: Mar. 8, 2024

(51) Int. Cl.
| | |
|---|---|
| G06T 19/00 | (2011.01) |
| G06F 3/01 | (2006.01) |
| G06F 40/58 | (2020.01) |
| G06T 13/20 | (2011.01) |
| G16H 20/70 | (2018.01) |

(52) U.S. Cl.
CPC ............. *G16H 20/70* (2018.01); *G06F 3/011* (2013.01); *G06F 40/58* (2020.01); *G06T 13/205* (2013.01); *G06T 19/006* (2013.01)

(58) Field of Classification Search
CPC ...... G06F 3/011; G06T 13/205; G06T 19/006
See application file for complete search history.

(56) References Cited

U.S. PATENT DOCUMENTS

| | | | | |
|---|---|---|---|---|
| 11,645,038 B1* | 5/2023 | Bond | ....................... | G06F 3/167 |
| | | | | 345/7 |
| 12,022,892 B2* | 7/2024 | Yamane | ................... | G08B 6/00 |
| 12,053,685 B2* | 8/2024 | Lockhart | ................. | G06F 3/013 |
| 2017/0365101 A1* | 12/2017 | Samec | .................. | G06T 19/006 |
| 2019/0384404 A1* | 12/2019 | Raghoebardajal | ........ | G06F 3/16 |
| 2020/0023157 A1* | 1/2020 | Lewis | ..................... | A61B 5/369 |
| 2020/0234827 A1* | 7/2020 | Internicola | .............. | G06F 3/011 |
| 2021/0312827 A1* | 10/2021 | Slater | ..................... | A61B 5/744 |
| 2022/0066207 A1* | 3/2022 | Croxford | ................ | G06F 40/40 |
| 2022/0139554 A1* | 5/2022 | Pillay | ..................... | G16H 70/20 |
| | | | | 705/2 |
| 2022/0351437 A1* | 11/2022 | Kondoh | ................ | G02B 27/017 |
| 2023/0123933 A1* | 4/2023 | Smith | ................... | A63F 13/217 |
| | | | | 345/419 |
| 2023/0267847 A1* | 8/2023 | Aldossari | ............... | G09B 19/00 |
| | | | | 434/236 |
| 2023/0298733 A1* | 9/2023 | Powers | ................ | A61B 5/0077 |
| | | | | 434/236 |

(Continued)

OTHER PUBLICATIONS

Kim et al., Virtual Reality Behavioral Therapy, 2016 (Year: 2016).*

*Primary Examiner* — Phong X Nguyen
(74) *Attorney, Agent, or Firm* — IP Consulting Group; Michael Razavi; Alfred Hoyte, Jr.

(57) ABSTRACT

A system for virtual therapy-based treatment of psychological issues is disclosed. The system receives a first input associated with a first scene via one or more sources. The system further extracts a set of audio signals associated with a set of objects within the first scene based on the received first input. The system further generates digital immersive content associated with the first scene based on the received first input and the extracted set of audio signals. The generated digital immersive content includes at least a first virtual object of a set of virtual objects associated with the set of objects and a first audio signal of the extracted set of audio signals. The system further renders the generated digital immersive content via a user platform. The user platform executes on the first user device associated with the first user.

20 Claims, 10 Drawing Sheets

(56) References Cited

U.S. PATENT DOCUMENTS

| | | | | |
|---|---|---|---|---|
| 2023/0389843 A1* | 12/2023 | Chung | ............... | A63F 13/67 |
| 2024/0152209 A1* | 5/2024 | Fung | ............... | G06F 3/011 |
| 2024/0282428 A1* | 8/2024 | Seth | ............... | G16H 50/20 |

* cited by examiner

VIRTUAL THERAPY-BASED APPARATUS AND METHOD FOR TREATMENT OF PSYCHOLOGICAL ISSUES

FIELD OF TECHNOLOGY

The present disclosure relates generally to computer vision, and more specifically to a virtual therapy-based treatment of psychological issues.

BACKGROUND

Psychological issues such as anxiety disorders, phobias, PTSD (Post-Traumatic Stress Disorder), depression, and addiction are prevalent worldwide and significantly impact the quality of life of an individual. Traditional therapeutic approaches such as cognitive-behavioral therapy (CBT) and exposure therapy have shown efficacy in treating these conditions. However, these methods often face limitations such as patient discomfort, limited accessibility, and difficulty in recreating realistic environments for exposure therapy.

Virtual reality (VR) technology has emerged as a promising tool in the field of mental health treatment. VR therapy provides a controlled, immersive environment that can simulate real-world scenarios, allowing therapists to expose patients to stimuli that trigger their symptoms in a safe and controlled manner. By gradually exposing patients to these stimuli, VR therapy facilitates desensitization and cognitive restructuring, leading to symptom reduction and improved coping mechanisms. Several studies have demonstrated the effectiveness of VR therapy across various psychological disorders. For example, VR exposure therapy has shown promising results in treating phobias such as fear of heights, flying, and public speaking. Additionally, VR-based mindfulness interventions have been effective in reducing stress and anxiety levels.

However, existing VR therapy systems often lack customization and flexibility, limiting their applicability across different psychological conditions and patient populations. Furthermore, the cost of VR equipment and software can be prohibitive for some healthcare providers and patients.

BRIEF SUMMARY OF THE DISCLOSURE

Systems and/or methods are provided for virtual therapy-based treatment of psychological issues, substantially as shown in and/or described in connection with at least one of the figures, as set forth more completely in the claims.

In accordance with an embodiment, there is provided a system for virtual therapy-based treatment of psychological issues. The system may be configured to receive a first input associated with a first scene via one or more sources. The system may be further configured to extract a set of audio signals associated with a set of objects within the first scene based on the received first input. The set of objects includes animated objects, in-animated objects, or a combination thereof. The system may be further configured to generate digital immersive content associated with the first scene based on the received first input and the extracted set of audio signals. The generated digital immersive content includes at least a first virtual object of a set of virtual objects associated with the set of objects and a first audio signal of the extracted set of audio signals The system may be further configured to render the generated digital immersive content via a user platform, wherein the user platform executes on a first user device associated with a first user.

In accordance with an embodiment, the one or more sources include the first user device.

In accordance with an embodiment, the at least one virtual object of the set of virtual objects is associated with the first user.

In accordance with an embodiment, the first user is suffering from one or more psychological issues.

In accordance with an embodiment, the digital immersive content assists in a treatment of one or more psychological issues associated with the first user.

In accordance with an embodiment, the system may be configured to identify a user platform to render the generated digital immersive content. The system may be further configured to render the digital immersive content via the identified user platform.

In accordance with an embodiment, the user platform corresponds to a virtual reality (VR) application.

In accordance with an embodiment, the user platform corresponds to one or more of a web platform, a metaverse platform, an augmented reality (AR) application, a mobile application, a holographic application, or a wearable device application.

In accordance with an embodiment, the system may be configured to determine first context information associated with the first scene based on the received first input. The first context information is indicative about a sensory feedback to be provided to the first user. The system may be further configured to control one or more sensors to provide sensory feedback to the first user based on the determined first context information associated with the first scene. The sensory feedback is provided while rendering the generated digital immersive content.

In accordance with an embodiment, the one or more sensors are embedded within a suit worn by the first user.

In accordance with an embodiment, the system may be configured to determine first context information associated with the first scene based on the received first input. The system may be further configured to determine environmental characteristics associated with the first scene based on the determined first context information. The system may be further configured to generate a first virtual scene in a virtual environment based on the determined environmental characteristics associated with the first scene and render the first virtual scene in the virtual environment, as the digital immersive content, via the identified user platform.

In accordance with an embodiment, the system may be configured to translate the first audio signal from a first language to a second language based on one or more preferences of the first user. The system may be further configured to render the generated digital immersive content via the user platform, wherein the generated digital immersive content comprises of the translated first audio signal.

In accordance with an embodiment, there is provided a method for virtual therapy-based treatment of psychological issues. The method includes receiving a first input associated with a first scene via one or more sources. The method further includes extracting a set of audio signals associated with a set of objects within the first scene based on the received first input. The set of objects includes animated objects, in-animated objects, or a combination thereof. The method further includes generating digital immersive content associated with the first scene based on the received first input and the extracted set of audio signals. The generated digital immersive content includes at least a first virtual object of a set of virtual objects associated with the set of objects and a first audio signal of the extracted set of audio signals. The method further includes rendering the generated digital immersive content via a user platform, wherein the user platform executes on a first user device associated with a first user.

In accordance with an embodiment, the one or more sources includes the first user device.

In accordance with an embodiment, the at least one virtual object of the set of virtual objects is associated with the first user.

In accordance with an embodiment, the first user is suffering from one or more psychological issues and the digital immersive content assists in a treatment of one or more psychological issues associated with the first user.

In accordance with an embodiment, the method further includes identifying a user platform to render the generated digital immersive content. The method further includes rendering the digital immersive content via the identified user platform.

In accordance with an embodiment, the user platform corresponds to one or more of a virtual reality (VR) application, a web platform, a metaverse platform, an augmented reality (AR) application, a mobile application, a holographic application, or a wearable device application.

In accordance with an embodiment, the method further includes determining first context information associated with the first scene based on the received first input. The first context information is indicative about a sensory feedback to be provided to the first user. The method further includes controlling one or more sensors to provide sensory feedback to the first user based on the determined first context information of the first scene, wherein the sensory feedback is provided while rendering the generated digital immersive content.

In accordance with an embodiment, the one or more sensors are embedded within a suit worn by the first user.

In accordance with an embodiment, the method further includes determining first context information associated with the first scene based on the received first input. The method further includes determining environmental characteristics associated with the first scene based on the determined first context information. The method further includes generating a first virtual scene in a virtual environment based on the determined environmental characteristics associated with the first scene and rendering the first virtual scene in the virtual environment, as the digital immersive content, via the identified user platform.

In accordance with an embodiment, the method further includes translating the first audio signal from a first language to a second language based on one or more preferences of the first user. The method further includes rendering the generated digital immersive content via the user platform, wherein the generated digital immersive content comprises of the translated first audio signal. In accordance with an embodiment, the translation of the first audio signal from the first language to the second language may correspond to a "real-time" translation or a "live" translation of the first audio signal from the first language to the second language. By way of example and not limitation, the disclosed method translates the first audio signal from the first language to the second language as soon as the first audio signal is spoken by the first virtual object of the set of virtual objects.

In accordance with an embodiment, there is provided a non-transitory computer-readable medium including computer program instructions, which when executed by a system, cause the system to perform one or more operations for virtual therapy-based treatment of psychological issues. The one or more operations include receiving a first input associated with a first scene via one or more sources. The one or more operations further include extracting a set of audio signals associated with a set of objects within the first scene based on the received first input. The set of objects includes animated objects, in-animated objects, or a combination thereof. The one or more operations further include generating digital immersive content associated with the first scene based on the received first input and the extracted set of audio signals. The generated digital immersive content includes at least a first virtual object of a set of virtual objects associated with the set of objects and a first audio signal of the extracted set of audio signals. The one or more operations further include rendering the generated digital immersive content via a user platform, wherein the user platform executes on a first user device associated with a first user.

The disclosed system may correspond to a revolutionary virtual reality (VR) therapy that may allow individuals to travel through time and experience corrective interactions. Such an approach may be applied to the past, present, and future to address various psychological issues. In an embodiment, the disclosed system may be utilized to facilitate healing and closure. For instance, patients can use the disclosed system to engage in conversations with deceased loved ones or reconnect with former partners to resolve unresolved emotions. By reliving these experiences and manipulating the outcomes through VR, individuals can achieve a sense of closure and emotional healing.

Moreover, the disclosed system may be effective in treating specific phobias, such as arachnophobia (fear of spiders), acrophobia (fear of heights), and the like. Using the disclosed system, users may be exposed to virtual spiders or virtual heights in a controlled environment. Such exposure therapy, combined with the immersive VR experience, may help users gradually overcome their fear of spiders or heights and alleviate their phobia.

Moreover, the disclosed system presents a distinctive solution tailored to users grappling with commitment-related challenges. Individuals encountering apprehension and indecision in committing to relationships and familial responsibilities may find solace in the disclosed system. Through simulated real-life scenarios, such as entering a household setting, participating in family meals, and interacting with virtual children who address the user as a parental figure, for instance, "mom" or "dad," the disclosed system offers immersive experiences. Furthermore, users may engage in dialogues with virtual spouses about daily occurrences. By affording a glimpse into the potential realities of committed partnerships, the disclosed system facilitates a gradual reduction of commitment-related fears and encourages users to envisage a gratifying future.

In summary, the disclosed system represents an innovative virtual reality (VR) platform designed to facilitate psychological interventions by enabling users to navigate through temporal scenarios and participate in corrective interactions. Whether the objective is to address historical traumas, mitigate phobias, or confront commitment-related anxieties, the disclosed system presents a pioneering methodology for enhancing mental health and fostering overall well-being.

DETAILED DESCRIPTION OF THE DISCLOSURE

Various aspects of the disclosure may be found in a method and system for virtual therapy-based treatment of psychological issues In light of the prevalence and impact of psychological issues worldwide, including anxiety disorders, phobias, PTSD (Post-Traumatic Stress Disorder), depression, and addiction, there is a recognized need for improved therapeutic approaches. While traditional methods like cognitive-behavioural therapy (CBT) and exposure therapy have demonstrated effectiveness, they encounter challenges such as patient discomfort, limited accessibility, and difficulties in recreating realistic environments for exposure therapy.

The emergence of virtual reality (VR) technology presents a promising avenue in the realm of mental health treatment. VR therapy offers a controlled, immersive environment capable of simulating real-world scenarios, thereby enabling therapists to expose patients to triggering stimuli in a safe and controlled manner. Through gradual exposure, VR therapy facilitates desensitization and cognitive restructuring, resulting in symptom reduction and enhanced coping mechanisms. Therefore, there is a need for a system that can simulate real-world scenarios and assist in the treatment of one or more psychological issues associated with a user suffering from one or more psychological issues.

Figure 1:
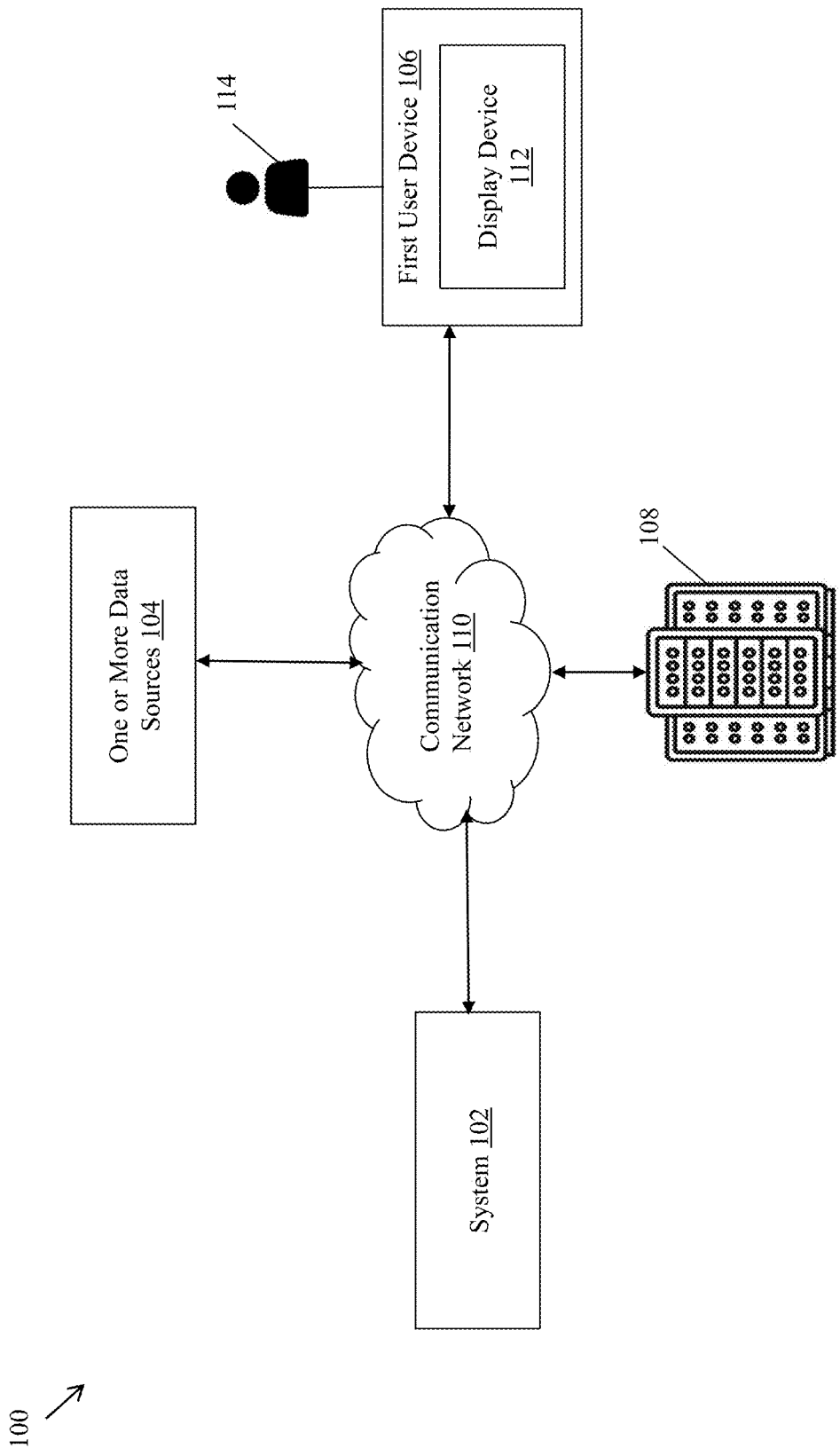
FIG. 1 is a block diagram that illustrates an exemplary environment for virtual therapy-based treatment of psychological issues, in accordance with an embodiment of the disclosure.

FIG. 1 is a block diagram that illustrates an exemplary environment for virtual therapy-based treatment of psychological issues, in accordance with an embodiment of the disclosure. Referring to FIG. 1, there is shown a network environment 100, which may include a system 102, one or more sources 104, a first user device 106, a server 108, and a communication network 110. With reference to FIG. 1, there is further shown a display device 112 and a first user 114 associated with the first user device 106.

The system 102 may comprise suitable logic, circuitry, interfaces, and/or code that may be configured to receive a first input associated with a first scene via the one or more sources 104. The system 102 may be further configured to extract a set of audio signals associated with a set of objects within the first scene based on the received first input. The system 102 may be further configured to generate digital immersive content associated with the first scene based on the received first input and the extracted set of audio signals. The system 102 may be further configured to render the generated digital immersive content via a user platform, wherein the user platform executes on the first user device 106 associated with the first user 114. Examples of the system 102 may include, but are not limited to, a computing device, a controller system, a server, a mainframe machine, a computer work-station, a smartphone, a cellular phone, a mobile phone, and/or a consumer electronic (CE) device.

The one or more sources 104 may comprise suitable logic, circuitry, interfaces, and/or code that may be configured to transmit the first input associated with the first scene. In an embodiment, the one or more sources 104 may include electronic devices (such as the first user device 106), systems, web servers, and the like. In another embodiment, the one or more sources 104 may include repositories that may store the set of audio signals. In another embodiment, the one or more sources 104 may include information associated with user accounts such as user social media accounts, transaction accounts, travel accounts, or the like.

The first user device 106 may include suitable logic, circuitry, interfaces, and/or code that may be configured to receive the digital immersive content from the system 102. The first user device 106 may be further configured to render the received digital immersive content on the display device 112. Examples of the first user device 106 may include, but are not limited to, a Head-Mounted Display (HMD), a Mobile VR Headset, an Augmented Reality (AR) Headset, a Mixed Reality (MR) Headset, a smartphone, a cellular phone, a mobile phone, a personal digital assistant (PDA) device, a tablet, a gaming device, a computing device, a mainframe machine, a server, a computer work-station, and/or a consumer electronic (CE) device.

The server 108 may include suitable logic, circuitry, interfaces, and/or code that may be configured to store the set of audio signals, and the digital immersive content. The server 108 may be configured to communicate with the system 102, the one or more sources 104, and the first user device 106 via the communication network 110. Examples of the server 108 may include, but are not limited to, an application server, a cloud server, a web server, a database server, a file server, a mainframe server, or a combination thereof.

In at least one embodiment, the server 108 may be implemented as a plurality of distributed cloud-based resources by use of several technologies that are well known to those ordinarily skilled in the art. A person with ordinary skill in the art will understand that the scope of the disclosure may not be limited to the implementation of the server 108 and the system 102 as two separate entities. In certain embodiments, the functionalities of the server 108 can be incorporated in its entirety or at least partially in the system 102, without a departure from the scope of the disclosure.

The communication network 110 may include a medium through which the system 102 may communicate with the one or more sources 104, the first user device 106, or the server 108. Examples of the communication network 110 may include, but are not limited to, the Internet, a cloud network, a Long Term Evolution (LTE) network, a Wireless Local Area Network (WLAN), a Local Area Network (LAN), a telephone line (POTS), or other wired or wireless network. Various devices in the network environment 100 may be configured to connect to the communication network 110, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), ZigBee, EDGE, IEEE 602.11, light fidelity (Li-Fi), 602.16, IEEE 602.11s, IEEE 602.11g, multi-hop communication, wireless access point (AP), a device to device communication, cellular communication protocols, or Bluetooth (BT) communication protocols, or a combination thereof.

The display device 112 may include suitable logic, circuitry, and interfaces that may be configured to display generated digital immersive content. The display device 112 may be a touch screen which may enable a user to provide a user-input via the display device 112. The touch screen may be at least one of a resistive touch screen, a capacitive touch screen, or a thermal touch screen. The display device 112 may refer to a display screen of a head-mounted device (HMD), a smart-glass device, a see-through display, a projection-based display, an electro-chromic display, or a transparent display. In accordance with an embodiment, the display device 112 may be realized through several known technologies such as, but not limited to, at least one of a Liquid Crystal Display (LCD) display, a Light Emitting Diode (LED) display, a plasma display, or an Organic LED (OLED) display technology, or other display devices.

In operation, the system 102 may be configured to receive the first input associated with the first scene. The first scene may refer to a scene that refers to a part of the story that takes place in a single location or setting, typically with continuous action. The first scene may be a fundamental unit of storytelling, characterized by its own narrative arc, visual composition, and emotional impact. The system 102 may be further configured to extract the set of audio signals associated with a set of objects within the first scene based on the received first input. In an embodiment, the set of objects may include animated objects, in-animated objects, or a combination thereof.

The animated objects may correspond to entities that may exhibit movement, typically through self-propulsion or manipulation by an external force. Examples of the animated objects include living organisms such as animals and humans, as well as mechanical devices like robots or animated characters in cartoons. The animated objects possess the capability to change position, shape, or orientation over time, either autonomously or in response to external stimuli. The in-animated objects lack this inherent ability to move on their own and remain static unless acted upon by an external force. Examples of in-animated objects include rocks, tables, buildings, and other non-living entities that do not exhibit spontaneous motion or behavior.

The system 102 may be further configured to generate digital immersive content associated with the first scene based on the received first input and the extracted set of audio signals. In an embodiment, the generated digital immersive content may include at least a first virtual object of a set of virtual objects associated with the set of objects and a first audio signal of the extracted set of audio signals. The system 102 may be further configured to render the generated digital immersive content via a user platform. The user platform may execute on the first user device 106 associated with the first user 114.

Figure 2:
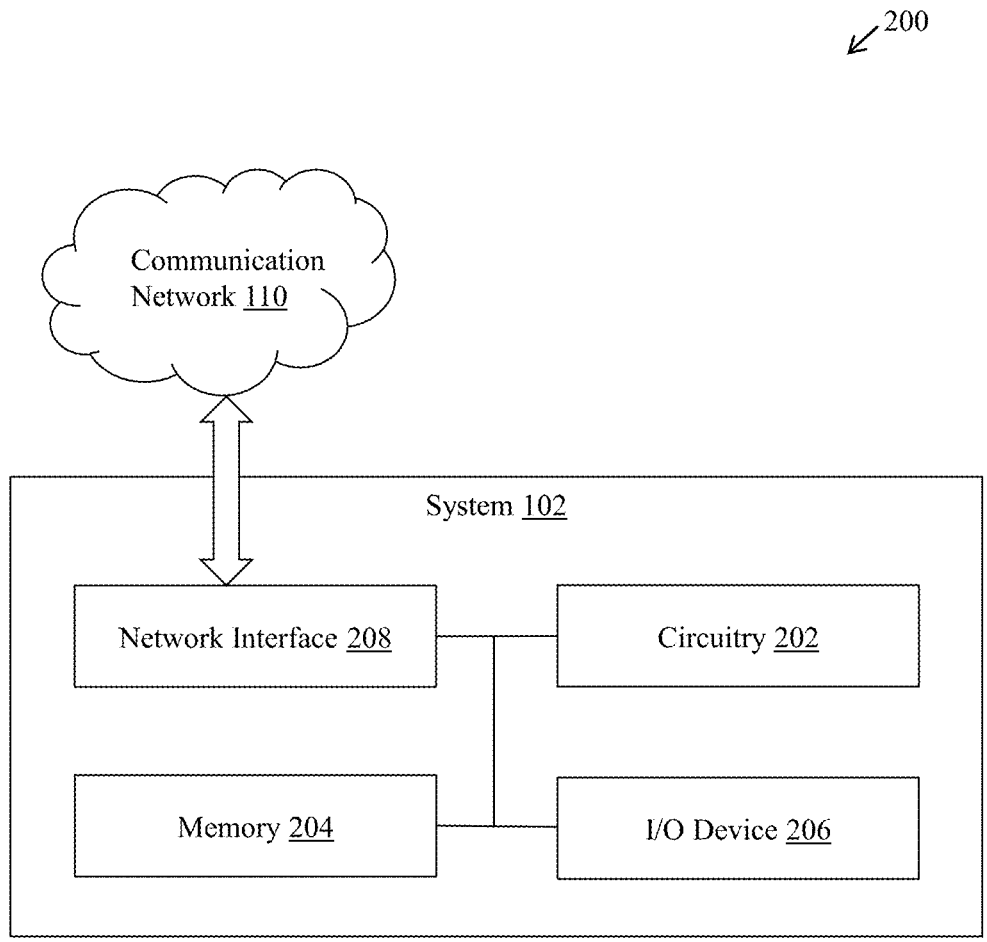
FIG. 2 is a block diagram that illustrates an exemplary system for virtual therapy-based treatment of psychological issues, in accordance with an embodiment of the disclosure.

FIG. 2 is a block diagram that illustrates an exemplary system for virtual therapy-based treatment of psychological issues, in accordance with an embodiment of the disclosure. FIG. 2 is explained in conjunction with elements from FIG. 1. With reference to FIG. 2, there is shown a block diagram 200 of the system 102. The system 102 may include a circuitry 202, a memory 204, an input/output (I/O) device 206, and a network interface 208. The circuitry 202 may be communicatively coupled to the memory 204, the I/O device 206, and the network interface 208.

The circuitry 202 may include suitable logic, circuitry, and interfaces that may be configured to execute program instructions associated with different operations to be executed by the system 102. For example, some of the operations may include, but are not limited to, receiving the first input, extracting the set of audio signals, generating the digital immersive content, and rendering the generated digital immersive content. The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other computing circuits.

The memory 204 may include suitable logic, circuitry, interfaces, and/or code that may be configured to store the program instructions to be executed by the circuitry 202. In at least one embodiment, the memory 204 may store the extracted set of audio signals. The memory 204 may also store the generated digital immersive content. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, and interfaces that may be configured to receive one or more user inputs and provide an output. For example, the system 102 may receive the user input via the I/O device 206. The I/O device 206 which includes various input and output devices, may be configured to communicate with the circuitry 202. Examples of the I/O device 206 may include, but are not limited to, a touch screen, a keyboard, a mouse, a joystick, a microphone, a display device (such as the display device 112), and a speaker.

The network interface 208 may include suitable logic, circuitry, and interfaces that may be configured to facilitate a communication between the circuitry 202, the one or more sources 104, the first user device 106, the display device 112, and the server 108, via the communication network 110. The network interface 208 may be implemented by use of various known technologies to support wired or wireless communication of the system 102 with the communication network 110. The network interface 208 may include, for example, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 208 may be configured to communicate via wireless communication with networks, such as the Internet, an Intranet, or a wireless network, such as a cellular telephone network, a public switched telephonic network (PSTN), a radio access network (RAN), a wireless local area network (LAN), and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 602.11a, IEEE 602.11b, IEEE 602.11g or IEEE 602.11n), voice over Internet Protocol (VOIP), light fidelity (Li-Fi), Worldwide Interoperability for Microwave Access (Wi-MAX), a protocol for email, instant messaging, and a Short Message Service (SMS).

The functions or operations executed by the system 102, as described in FIG. 2, may be performed by the circuitry 202. Various operations executed by the circuitry 202 are described in detail, for example, in FIGS. 3, 4, 9, and 10.

Figure 3:
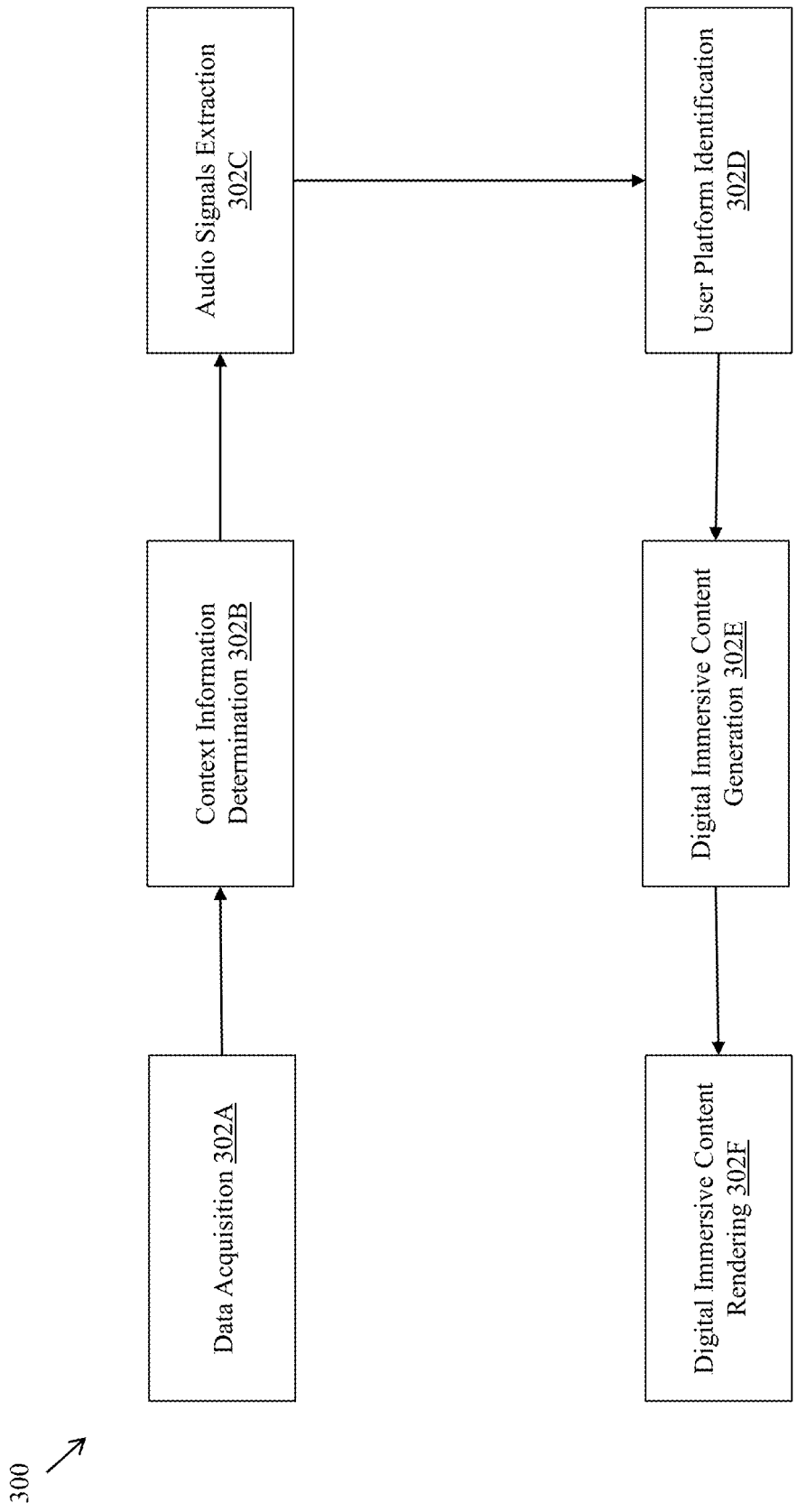
FIG. 3 is a diagram that illustrates exemplary operations for virtual therapy-based treatment of psychological issues, in accordance with an embodiment of the disclosure.

FIG. 3 is a diagram that illustrates exemplary operations for virtual therapy-based treatment of psychological issues, in accordance with an embodiment of the disclosure. FIG. 3 is explained in conjunction with elements from FIG. 1 and FIG. 2. With reference to FIG. 3, there is shown a block diagram 300 that illustrates exemplary operations from 302A to 302F, as described herein. The exemplary operations illustrated in the block diagram 300 may start at 302A and may be performed by any computing system, apparatus, or device, such as by the system 102 of FIG. 1 or circuitry 202 of FIG. 2. Although illustrated with discrete blocks, the exemplary operations associated with one or more blocks of the block diagram 300 may be divided into additional blocks, combined into fewer blocks, or eliminated, depending on the particular implementation.

At 302A, a data acquisition operation may be performed. In data acquisition operation, the circuitry 202 may be configured to receive a first input associated with a first scene. The first input may be received from the first user 114 via the one or more sources 104. The first user 114 may be, for example, a patient who may be suffering from psychological issues. The psychological issues faced by the first user 114 may include a wide range of mental health conditions. Such conditions may affect the thoughts, perceptions, feelings, and behaviours of the first user 114, and may lead to difficulties in coping with work, relationships, and other demands. Examples of such psychological issues may include, but are not limited to, anxiety disorders, depression, post-traumatic stress disorder (PTSD), psychosis, schizophrenia, bipolar affective disorder, obsessive-compulsive disorder (OCD), eating disorders, and personality disorders.

In an embodiment, the first scene may be a fundamental unit of storytelling, characterized by its own narrative arc, visual composition, and emotional impact. The first scene may have to be recreated as the digital immersive content with virtual objects. As a first example, the first user 114 may be suffering from depression because of the recent demise of his/her parents in a car accident. The user and his/her parents might have been traveling in a car when they might have encountered the accident in which his/her parents might have died. From that point onwards, the first user 114 might be suffering from depression and might be taking counselling lessons from a doctor.

In an embodiment, the first input may include photos and videos to recreate the interior and exterior of the patient's house or the specific location where the experience needs to take place in virtual therapy.

In an embodiment, the first input may be received from a user device of the doctor (who may be a therapist) or the user device associated with the first user 114. In an embodiment, the user input may be provided in a variety of ways such as textual input, voice input, and the like. The first user input may include details about the first scene like what was happening in the first scene, how many characters were there in the first scene, what was being discussed in the first scene, environmental characteristics (like weather conditions) associated with the first scene, and the like.

At 302B, a context information determination operation may be executed. In the context information determination operation, the system 102 may be configured to determine first context information associated with the first scene. The first context information associated with the first scene may be indicative of a first context of the first scene. In an embodiment, the first context information associated with the first scene may be determined based on the received first input. The first context of the first scene may refer to the circumstances, setting, and background information that surround the events or actions taking place within it. The first context may encompass various elements that may establish an atmosphere, mood, and significance of the first scene, providing important context for understanding the characters' motivations and the overall narrative. Furthermore, the first context of the first scene may also include information about the physical environment in which the first scene occurs, such as the time, location, and surroundings, information about the characters in the first scene, information about the emotional tone of the first scene and the feelings and moods it evokes, and the like. In an embodiment, the first context of the scene first may be determined to provide sensory feedback to the first user 114 while viewing the digital immersive content associated with the first scene.

In an embodiment, the system 102 may be configured to analyze the photos and videos of themselves and the individuals they need to interact with in VR based on the first input. The system 102 may further create realistic VR avatars for the therapist and patient to use during the VR therapy session.

At 302C, an audio signals extraction operation may be executed. In the audio signals operation, the circuitry 202 may be configured to extract a set of audio signals. The set of audio signals may be associated with a set of objects that may be present in the first scene. The set of objects may include animated objects, in-animated objects, or a combination thereof. As discussed above, the animated objects may correspond to entities that may exhibit movement, typically through self-propulsion or manipulation by an external force. Examples of the animated objects include living organisms such as animals and humans, as well as mechanical devices like robots or animated characters in cartoons. The animated objects possess the capability to change position, shape, or orientation over time, either autonomously or in response to external stimuli. The in-animated objects lack this inherent ability to move on their own and remain static unless acted upon by an external force. Examples of in-animated objects include rocks, tables, buildings, and other non-living entities that do not exhibit spontaneous motion or behavior.

In an embodiment, the system 102 may be configured to extract the set of audio signals. The set of audio signals may be extracted based on the received first input. In an embodiment, the system 102 may be configured to extract the set of audio signals from the one or more sources 104. The set of audio signals may correspond to the voices of the animated objects (such as the voice of a person, or the barking sound of a dog) or sounds associated with inanimate objects (such as the sound of a door opening or closing, or sound of rain and the like).

In an embodiment, the system 102 may be configured to extract the set of audio signals from the one or more sources 104. As discussed above, the one or more sources 104 may include first user accounts may include user social media accounts, transaction accounts, travel accounts, or the like. As an example, if the audio signal is associated with an object (say a friend of the first user 114), then the system 102 may be configured to extract audio signals from videos of the friend of the first user 114. Such videos may be uploaded/posted on the social media accounts of the first user 114. In another embodiment, the sound of the in-animated objects like the sound of rain may be extracted from web sources (like audio repositories) included in the one or more sources 104.

In an embodiment, a voice engineer may extract the voices of the individuals in the provided videos and use AI-based voice cloning technology to replicate their voices. This will allow for realistic and immersive conversations during the VR therapy. The voice engineer can also incorporate live translation if needed.

At 302D, a user platform identification operation may be executed. In the user platform execution operation, the system 102 may be configured to identify a user platform to render the digital immersive content. The user platform may receive the digital immersive content and may provide the digital immersive content to the first user 114. The user platform may include one or more processors that, based on being configured by an application or other software, configure the user platform to provide the digital immersive content for consumption by the first user 114. The first user 114 may be able to control the display or output of the consumable content via the user platform such as by playing, stopping, pausing, adjusting, or otherwise interacting with the digital immersive content via the user platform. Examples of the user platform may include, but are not limited to, a virtual reality (VR) application, a metaverse platform, an augmented reality (AR) application, a web platform, a mobile application, a holographic application, or a wearable device application.

At 302E, a digital immersive content generation operation may be performed. In the digital immersive content generation operation, the system 102 may be configured to generate the digital immersive content associated with the first scene based on the received first input and the extracted set of audio signals. In another embodiment, the system 102 may be configured to generate the digital immersive content associated based on the identified user platform. Specifically, the digital immersive content may be customized for the user platform.

The digital immersive content may refer to media experiences that fully engage the senses of the viewer or participant (such as the first user 114), creating a feeling of being physically present in a simulated environment. Such type of digital immersive content may leverage technologies such as virtual reality (VR), augmented reality (AR), mixed reality (MR), and 360-degree video to provide users with highly interactive and immersive experiences to the viewer. In an embodiment, the digital immersive content may correspond to a virtual or simulated re-creation of the first scene using computer graphics techniques.

Examples of digital immersive content may include Virtual Reality (VR) content, Augmented Reality (AR) content, Mixed Reality (MR) content, and 360-Degree Video. The VR technology creates fully immersive digital environments that users can explore and interact with using a head-mounted display (HMD) and motion-tracking controllers. Such VR experiences may range from realistic simulations of real-world environments to fantastical, imaginary worlds. In the AR content, digital elements are overlaid in the real world, typically viewed through a smartphone or AR glasses. The AR content may enhance the viewer's perception of the physical environment by adding digital objects, information, or interactive elements. The MR may combine the elements of both VR and AR, thereby allowing digital objects to interact with the real world and vice versa. The MR experiences often involve wearing a headset that integrates virtual and real-world elements seamlessly. The 360-Degree Video format may capture footage in all directions simultaneously, allowing viewers to control their perspective and explore the environment as if they were physically present. Such 360-degree videos are typically viewed on VR headsets, smartphones, or computers.

In an embodiment, the generated digital immersive content may include a set of virtual objects that may be associated with the set of objects. Each virtual object of the set of virtual objects may refer to digital representations of the corresponding objects or entities that may exist solely within the digital immersive content. It may be noted that such virtual objects may not be physically tangible but are instead created using computer graphics and displayed on a screen or through virtual reality (VR) or augmented reality (AR) devices based on the user platform associated with the user device of the viewer (or the first user 114).

With reference to the first example, the generated digital immersive content may include a first virtual object associated with the first user 114, a second virtual object associated with a father of the first user 114, a third virtual object associated with a mother of the first user 114, and a fourth virtual object associated with the car.

In an embodiment, the system 102 may be configured to include the extracted set of audio signals in the digital immersive content. Specifically, the system 102 may be configured to the tie the audio signal with the corresponding object along with the action. For example, the voice of the friend of the first user 114 may be linked (or tied) to the virtual object associated with the friend of the user and may be rendered when the virtual object associated with the friend of the first user speaks (i.e. performs an action). Similarly, the sound of the door opening may be done when the virtual object corresponding to the door opens (i.e. performs an action).

In another embodiment, the generated digital immersive content may further include special effects based on the environmental characteristics associated with the first scene. For example, it may be raining in the generated digital immersive and the audio signals associated with raining may be included in the generated digital immersive content. Other examples of the special effects may include the addition of a virtual object associated with smoke, a virtual object associated with sand, a virtual object associated with dust, a virtual object associated with water, and the like in the digital immersive content.

At 302F, a digital immersive content rendering operation may be executed. In the digital content rendering operation, the system 102 may be configured to render the generated digital immersive content on the user platform. As discussed above, the user platform may execute on the first user device 106 associated with the first user 114.

In an embodiment, the system 102 may be configured to control one or more sensors to provide sensory feedback to the first user 114 based on the determined first context of the first scene. In an embodiment, the sensory feedback may be provided to the first user 114 while rendering the digital immersive content on the user platform. The one or more sensors may be embedded within a suit (such as a Tesla® suit or a shock suit) that may worn by the first user 114 while viewing the digital immersive content. Such a suit may allow patients who may be soldiers with PTSD to re-experience trauma they might have faced earlier. In another embodiment, such a suit may also be used with individuals who might have experienced a gunshot.

For example, the first user 114 may be a soldier who may be suffering from PTSD because he/she might have been in a war scenario. The user may provide the first input associated with a first scene that may correspond to the war scenario. The system 102 may generate the digital immersive content associated with the war scenario. During rendering the digital immersive content, the first user 114 may experience physical touch or even bullets through the suit.

In an embodiment, a special effects technician may create sensory experiences during the VR therapy. They will use various machines and techniques to replicate the environment needed to recreate the patient's (the first user 114) past experiences or provide the necessary sensations for treatment. This can include weather machines to simulate wind, heat, rain, or dust, as well as creating physical sensations like falling pieces, explosions, smoke, and more.

Figure 5:
FIG. 5 is a diagram that illustrates exemplary second digital immersive content, in accordance with an embodiment of the disclosure.

In an embodiment, the rendering of the digital immersive content with or without the sensory feedback may assist in the treatment of one or more psychological issues associated with the first user 114. With reference to the first example, in the digital immersive content, the first user 114 may have a final conversation with his/her parents before the accident. Such conversation might change the emotional state of the first user 114 which may eventually assist in the treatment of one or more psychological issues associated with the first user 114. The system 102 may be further configured to generate the digital immersive content associated with the scenario discussed in the first example as provided in the FIG. 5. In the digital immersive content shown in FIG. 5, the first user 114 may be seen interacting with a personality (specifically an avatar of the personality) on the first user device 106.

In an embodiment, the system 102 may be configured to translate the first audio signal of the set of audio signals from a first language (say French) to a second language (say English) based on one or more preferences of the first user. The system 102 may be further configured to render the generated digital immersive content via the user platform. The generated digital immersive content may include the translated first audio signal.

Figure 6:
FIG. 6 is a diagram that illustrates exemplary third digital immersive content, in accordance with an embodiment of the disclosure.

In an embodiment, the system 102 may be configured to generate the digital immersive environment based on information about the interior and the exterior of the specific location where the experience needs to take place in the virtual therapy. Such information may be included in the first input. For example, the first user 114 may provide images and videos of a portion of a building (such as interior of a house). Based on the provided images and videos, the system 102 may generate the digital immersive environment that may be similar to the images and videos of the portion of the building as shown in FIG. 6.

In an exemplary scenario, the therapist may engage in weekly psychotherapy sessions with the patient for a period of 2-4 months, or until the specific issues are identified by the therapist. The patient will be mentally prepared for the abut the virtual therapy by receiving a detailed explanation of what the experience will involve, what to anticipate, and the potential emotions that may arise before, during, and after the virtual therapy. Following the virtual therapy experience, the therapist may continue with psychotherapy for an additional few weeks to process the experience and ensure that the patient is in a comfortable and healthy mental state. This post-virtual therapy aims to support the patient in integrating and understanding the insights gained from the TSM, promoting long-term healing and growth.

Figure 7:
FIG. 7 is a diagram that illustrates an exemplary avatar of an exemplary user in an exemplary immersive media content, in accordance with an embodiment of the disclosure.

In the entire process of virtual therapy, the therapist may conduct weekly therapy sessions to identify the specific areas of concern for the patient. For patients seeking to heal past experiences, they will be asked to provide photos and videos of the individuals they need to interact with, as well as the locations where these experiences took place as discussed in the data acquisition operation 302A. This may allow for the replication of these past experiences in the virtual therapy. However, if the therapy is focused on addressing present or future fears and phobias, the patient may not need to provide specific photos and videos. Instead, the system may create a virtual environment, such as a random house, to simulate these experiences based on the description provided by the patient. Based on the description, the system 102 may be configured to create the immersive virtual reality environment and ensure that the virtual therapy that may be effective and impactful. In an exemplary scenario, the therapist and patient may collaborate with a team of professionals, including architects, VR/AI avatar engineers, AI sound engineers, and special effects technicians to create the virtual environment, and avatars, generate sounds, and include special effects in the virtual environment respectively. An example of such avatar of a user in the generated digital immersive content is shown in FIG. 7.

Figure 4:
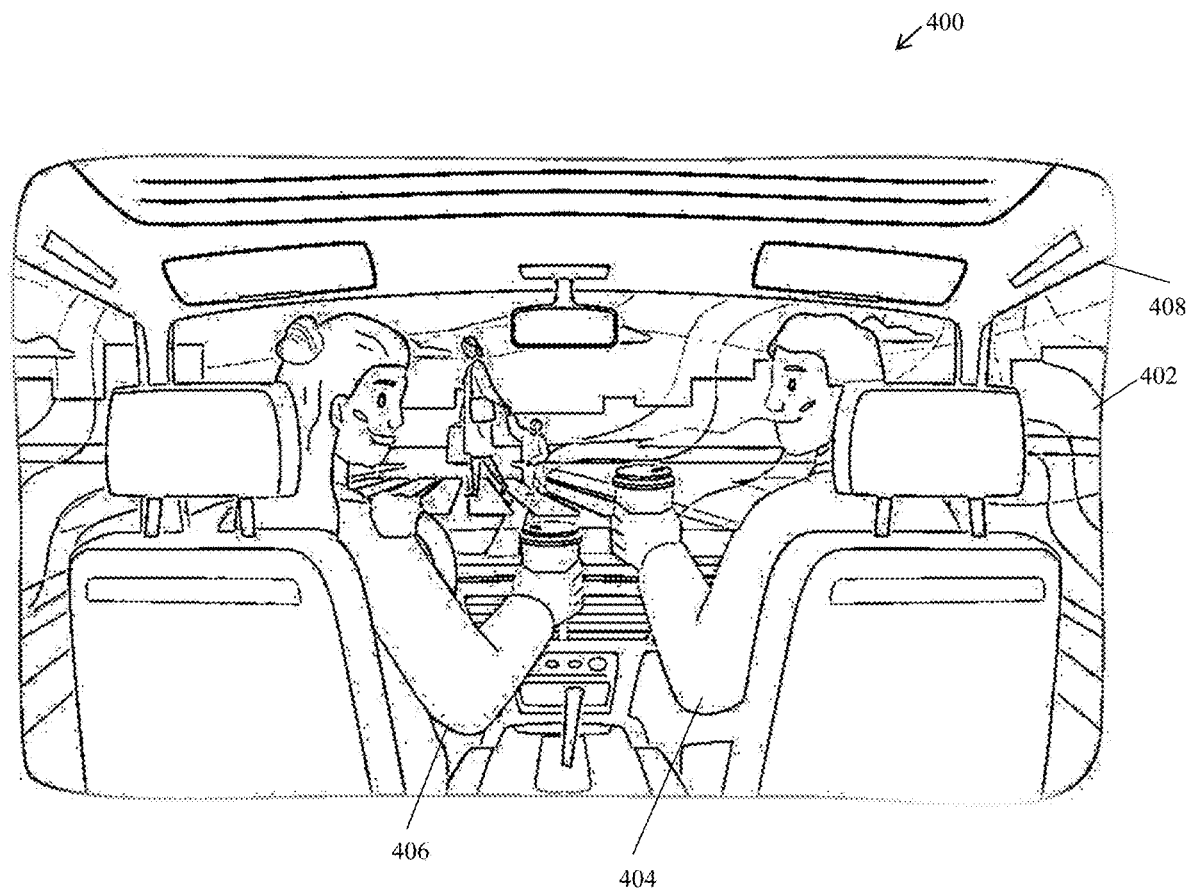
FIG. 4 is a diagram that illustrates exemplary first digital immersive content, in accordance with an embodiment of the disclosure.

FIG. 4 is a diagram that illustrates exemplary first digital immersive content, in accordance with an embodiment of the disclosure. FIG. 4 is explained in conjunction with elements from FIGS. 1, 2, and 3. With reference to FIG. 4, there is shown an exemplary scenario 400. There is further shown digital immersive content 402 that may include a first virtual object 404, a second virtual object 406, and a third virtual object 408.

In an embodiment, the system 102 may be configured to receive, via one or more sources 104, a first input associated with a first scene in which the first user 114 may be sitting with his/her parents in a car before a car accident as described in the first example in FIG. 3. The system 102 may be configured to extract a set of audio signals associated with a set of objects within the first scene based on the received first input. The set of objects may include a digital avatar of the father of the first user 114, the mother of the first user 114, and the car in which the father and the mother of the first user 114 may have been traveling before they encountered an accident.

The system 102 may be further configured to generate the digital immersive content 402 associated with the first scene based on the received first input and the extracted set of audio signals. The generated digital immersive content may include the first virtual object 404, the second virtual object 406, and the third virtual object 408. In an embodiment, the digital immersive content 402 may further include audio signals associated with the father of the first user 114 that may be rendered when the first virtual object 404 speaks. Similarly, the digital immersive content 402 may further include audio signals associated with the mother of the first user 114 that may be rendered when the second virtual object 406 speaks. The digital immersive content 402 may further include audio signals associated with the car in motion.

The system 102 may be further configured to render the generated digital immersive content 402 via the user platform. As discussed above, the user platform may execute on the first user device 106 associated with the first user 114. Furthermore, the generated digital immersive content 402 when watched by the first user 114 may assist in a treatment of one or more psychological issues associated with the first user 114.

Figure 8:
FIG. 8 is a diagram that illustrates an exemplary user wearing a suit that provides sensory feedback to the exemplary user, in accordance with an embodiment of the disclosure.

In an embodiment, on the day of the VR-Therapy session, the first user 114 may enter a dedicated VR room. Both the patient and therapist may wear VR headsets equipped with an emotion tracking system as shown in FIG. 8. Additionally, they will have the option to wear a suit (such as a Tesla® suit or a shockwave suit) to enhance the sensory experience. In an embodiment, the suit may provide a full body haptic feedback to the first user 114 using electro muscle stimulation (EMS) and transcutaneous electrical nerve stimulation (TENS) to simulate a range of real-life feelings and sensations to the first user 114. In an embodiment, the suit may provide a physical feedback based on the digital immersive content that may be experienced on the first user device 106. In an alternate embodiment, the suit may be capable of providing a Haptic Feedback to the first user 114 by using one or more Inertial Measurement Unit (IMU) sensors embedded in the suit.

During the session, the therapist may appear as an avatar that resembles the person the patient needs to interact with, such as their mother. The first user 114 either appears as themselves or as an avatar representing their younger self, depending on the therapy goals discussed in previous sessions. AI-based technology may be used to generate the voice of the person the first user 112 needs to interact with, ensuring a realistic and immersive experience. If the person the patient needs to interact with speaks a different language, immediate voice translation can be added to the experience, along with voice cloning as discussed in FIG. 3.

In an alternate embodiment, the therapist and first user 114 may sit in separate rooms. The therapist may connect with the patient via an electronic device (say a phone or an earpiece) and may impersonate the individual the patient needs to communicate with using the AI-based voice cloning technology. The therapist may assess if special effects would be beneficial. If so, the patient may experience special effects such as rain, dust, sand, etc., to make the therapeutic experience more realistic.

In case the patient is bedridden, the system 102 may be configured to generate a hologram of a person with whom they can interact. Specifically, the system 102 may generate the hologram for bedridden patients with a terminal illness. The system 102 may correspond to a holobox, which may be configured to generate a holographic visualization of a person, a product, a logo, or the like. The disclosed system 102 that may correspond to the holobox may be combined with AI-based voice cloning for the therapist to use with the first user 114. Such a method may be ideal for bedridden individuals as it can be executed without the need for VR headsets, special glasses, or physical movement and may be experienced with the naked eye. Also, the portable holobox can be taken to the hospital and placed in front of the patient. The patient sees their loved one in the holobox, and the therapist uses the voice mimicking to communicate with the patient.

For example, the therapist may be working with an 83-year-old female patient with a terminal illness who may fear death due to the unknowns of the afterlife. The disclosed system may provide feelings of safety by creating a hologram of her deceased husband. The therapist can have therapeutic conversations with the patient through the hologram, with the hologram of her husband reassuring her that she will be safe and expressing his love for her. As another example, the therapist may be working with a young girl with a terminal illness. In this case, angels may be created in the holobox to explain to her what heaven looks like and how happy she will be there. This illusion of control and safety in the afterlife may help reduce fear.

In another embodiment, the disclosed system 102 that creates a hologram may also be used for visually impaired individuals. The hologram-based haptic technology allows the first user 114 to touch and feel the hologram, not just see it. In an embodiment, the patient may provide a video of the individual they need to interact with, and the system 102 may create a haptic hologram of their face. Details about the extraction of voice are provided, for example, in FIG. 3. The visually impaired patient remains stationary and physically touches the hologram to feel the face of the individual they need to interact. The therapist communicates with the patient as if embodying the individual they need to interact with.

Figure 9:
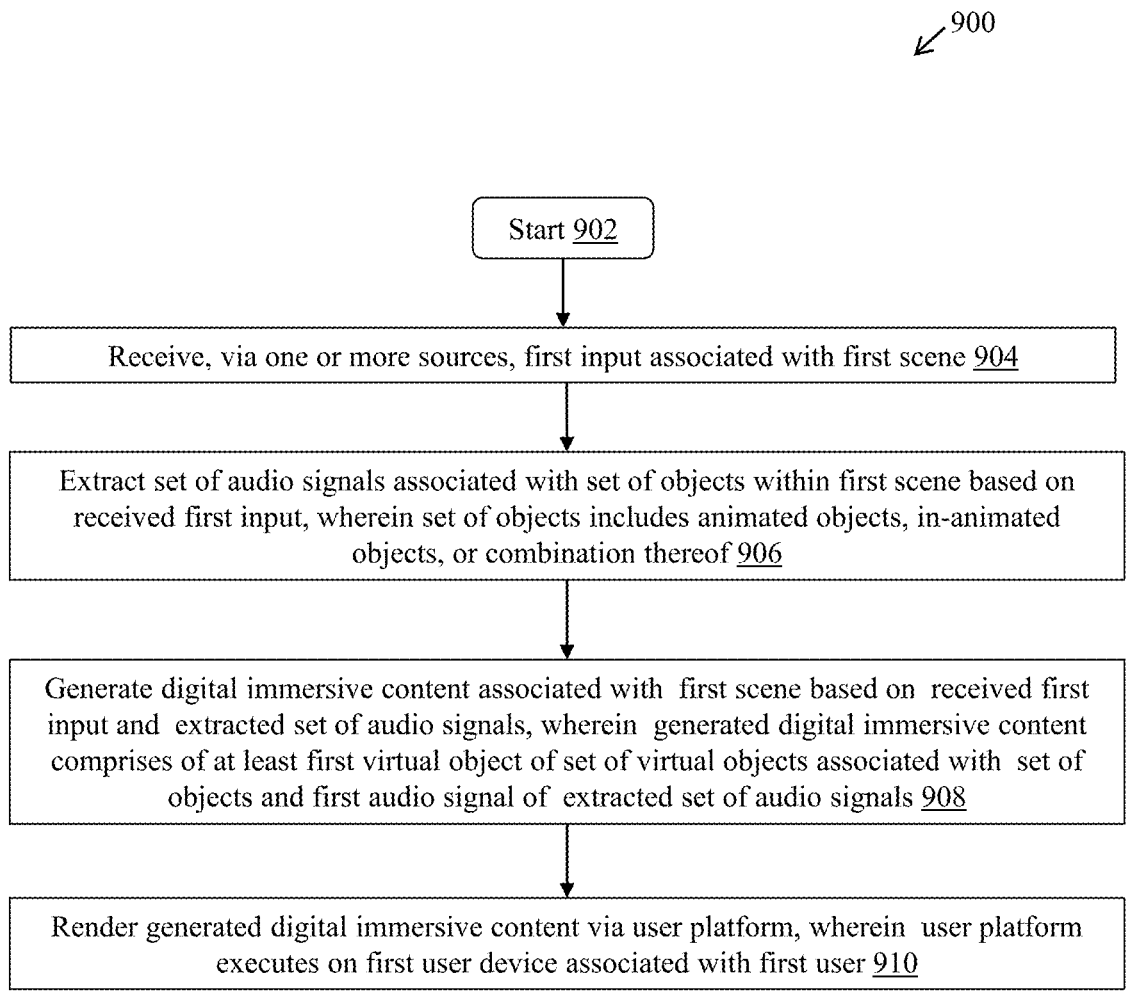
FIG. 9 is a flowchart that illustrates an exemplary method for virtual therapy-based treatment of psychological issues, in accordance with an embodiment of the disclosure.

FIG. 9 is a flowchart that illustrates an exemplary method for virtual therapy-based treatment of psychological issues, in accordance with an embodiment of the disclosure. FIG. 9 is explained in conjunction with elements from FIGS. 1, 2, 3, and 4. With reference to FIG. 9, there is shown a flowchart 900. The operations of the exemplary method may be executed by any computing system, for example, by the system 102 of FIG. 1 or the circuitry 202 of FIG. 2. The operations of the flowchart 900 may start at 902 and may proceed to 904.

At 904, the first input associated with the first scene may be received via the one or more sources 104. In at least one embodiment, the circuitry 202 may receive, via the one or more sources 104, the first input associated with the first scene. Details about the reception of the first scene are provided, for example, in FIG. 3.

At 906, the set of audio signals may be extracted based on the received first input. The set of audio signals may be associated with a set of objects within the first scene. The set of objects may include the animated objects, the in-animated objects, or a combination thereof. In at least one embodiment, the circuitry 202 may extract the set of audio signals associated with the set of objects within the first scene based on the received first input, wherein the set of objects includes the animated objects, the in-animated objects, or a combination thereof. Details about the set of objects are provided, for example, in FIG. 3.

At 908, the digital immersive content 402 associated with the first scene may be generated based on the received first input and the extracted set of audio signals. The generated digital immersive content 402 includes at least a first virtual object 404 of a set of virtual objects associated with the set of objects and a first audio signal of the extracted set of audio signals. In at least one embodiment, the circuitry 202 may generate the digital immersive content 402 associated with the first scene based on the received first input and the extracted set of audio signals, wherein the generated digital immersive content 402 includes at least the first virtual object 404 of the set of virtual objects associated with the set of objects and a first audio signal of the extracted set of audio signals.

At 910, the generated digital immersive content 402 may be rendered via the user platform. The user platform executes on a first user device 106 associated with the first user 114. In at least one embodiment, the circuitry 202 may render the generated digital immersive content 402 via the user platform, wherein the user platform executes on the first user device 106 associated with the first user 114. Control may pass to the end.

Figure 10:
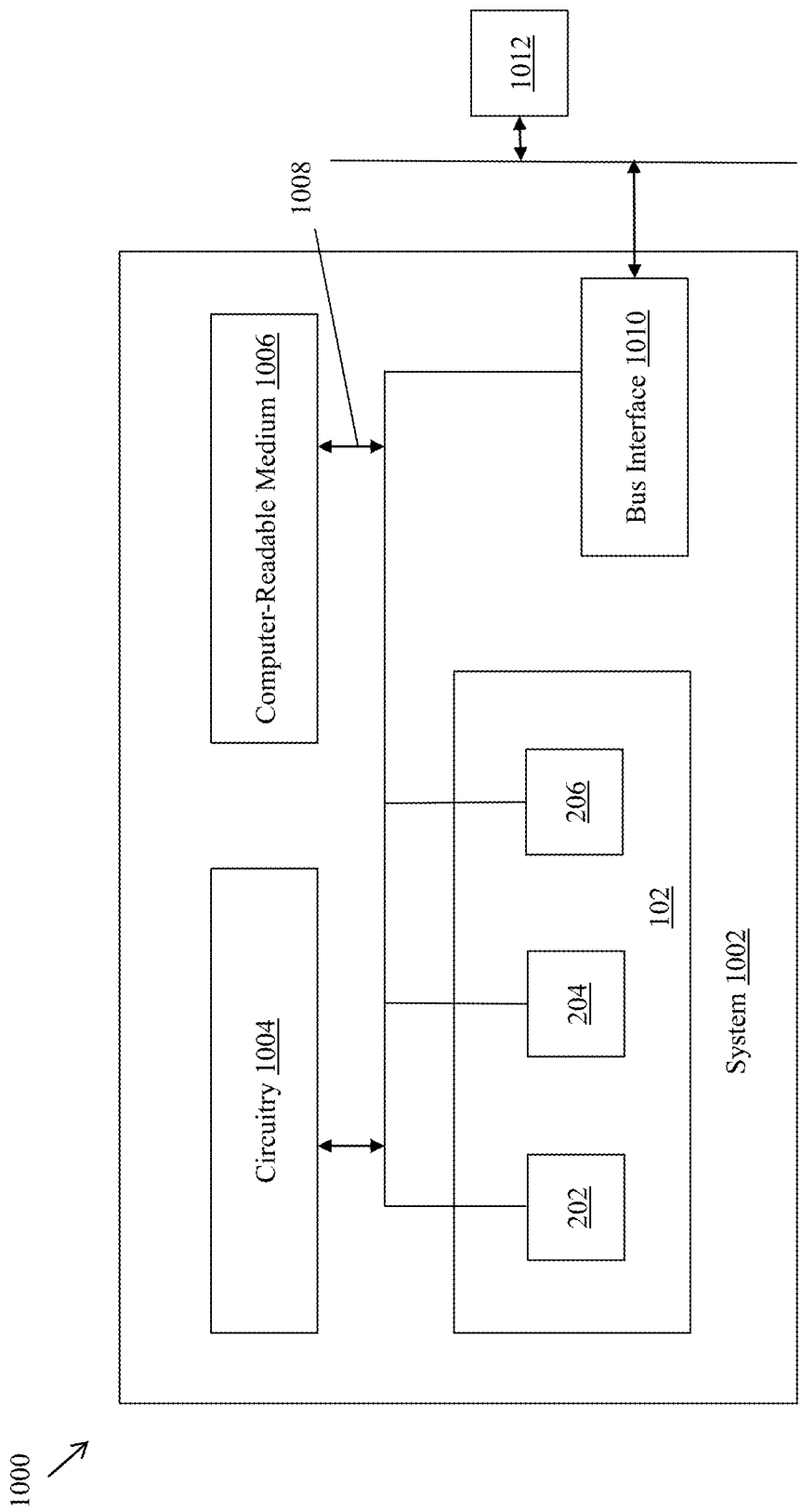
FIG. 10 is a conceptual diagram illustrating an example of a hardware implementation for a system used for virtual therapy-based treatment of psychological issues, in accordance with an embodiment of the disclosure.

FIG. 10 is a conceptual diagram illustrating an example of a hardware implementation for a system used for virtual therapy-based treatment of psychological issues, in accordance with an embodiment of the disclosure. FIG. 10 is explained in conjunction with elements from FIGS. 1, 2, 3, 4, and 9. Referring to FIG. 10, the hardware implementation shown by a representation 1000 for the network environment 100 employs a processing system 1002 for virtual therapy-based treatment of psychological issues, in accordance with an embodiment of the disclosure, as described herein.

In some examples, the processing system 1002 may comprise a circuitry 1004, a non-transitory computer-readable medium 1006, a bus 1008, a bus interface 1010, and a transceiver 1012.

The circuitry 1004, such as the circuitry 202, may be configured to manage the bus 1008 and general processing, including the execution of a set of instructions stored on the non-transitory computer-readable medium 1006. The set of instructions, when executed by the circuitry 1004, causes the system 102 to execute the various functions described herein for any particular apparatus. The circuitry 1004 may be implemented, based on a number of processor technologies known in the art. Examples of the circuitry 1004 may be RISC processor, ASIC processor, CISC processor, and/or other processors or control circuits.

The non-transitory computer-readable medium 1006 may be used for storing data that is manipulated by the circuitry 1004 when executing the set of instructions. The data is stored for short periods or in the presence of power.

The bus 1008 may be configured to link together various circuits. In this example, the network environment 100 employing the processing system 1002 and the non-transitory computer-readable medium 1006 may be implemented with bus architecture, represented generally by bus 1008. The bus 1008 may include any number of interconnecting buses and bridges depending on the specific implementation of the system 102 and the overall design constraints. The bus interface 1010 may be configured to provide an interface between the bus 1008 and other circuits, such as the transceiver 1012, and external devices, such as the display device 112, and the server 108.

The transceiver 1012 may be configured to provide a communication of the system 102 with various other apparatus, such as the display device 112, via a network. The transceiver 1012 may communicate via wireless communication with networks, such as the Internet, the Intranet and/or a wireless network, such as a cellular telephone network, a wireless local area network (WLAN) and/or a metropolitan area network (MAN). The wireless communication may use any of a plurality of communication standards, protocols and technologies, such as 5th generation mobile network, Global System for Mobile Communications (GSM), Enhanced Data GSM Environment (EDGE), Long Term Evolution (LTE), wideband code division multiple access (W-CDMA), code division multiple access (CDMA), time division multiple access (TDMA), Bluetooth, Wireless Fidelity (Wi-Fi) (such as IEEE 602.11a, IEEE 602.11b, IEEE 602.11g and/or IEEE 602.11n), voice over Internet Protocol (VOIP), and/or Wi-MAX.

It should be recognized that, in some embodiments of the disclosure, one or more components of FIG. 10 may include software whose corresponding code may be executed by at least one processor, for across multiple processing environments.

In an aspect of the disclosure, the circuitry 1004, the non-transitory computer-readable medium 1006, or a combination of both may be configured or otherwise specially programmed to execute the operations or functionality of the circuitry 202, the memory 204, the I/O device 206, and the network interface 208 or various other components described herein, as described with respect to FIGS. 1 to 10.

Various embodiments of the disclosure comprise the system 102 for virtual therapy-based treatment of psychological issues. The system 102 may comprise, for example, the circuitry 202, the memory 204, the I/O device 206, and the network interface 208. The circuitry 202 of the system 102 may be configured to receive the first input associated with the first scene via the one or more sources 104. The circuitry 202 may be further configured to extract the set of audio signals associated with the set of objects within the first scene based on the received first input. The set of objects includes animated objects, in-animated objects, or a combination thereof. The circuitry 202 of the system 102 may be further configured to generate the digital immersive content 402 associated with the first scene based on the received first input and the extracted set of audio signals. The generated digital immersive content 402 may include at least a first virtual object of a set of virtual objects associated with the set of objects and a first audio signal of the extracted set of audio signals. The circuitry 202 of the system 102 may be further configured to render the generated digital immersive content via a user platform. The user platform executes on the first user device 106 associated with the first user 114.

As utilized herein, the term "exemplary" means serving as a non-limiting example, instance, or illustration. As utilized herein, the terms "for example," and "for example" set off lists of one or more non-limiting examples, instances, or illustrations. As utilized herein, circuitry is "operable" to perform a function whenever the circuitry comprises the necessary hardware and/or code (if any is necessary) to perform the function, regardless of whether performance of the function is disabled, or not enabled, by some user-configurable setting.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (for example, application specific integrated circuits (ASICs)), by program instructions being executed by one or more processors, or by a combination of both.

Additionally, these sequences of actions described herein can be considered to be embodied entirely within any non-transitory form of computer readable storage medium having stored therein a corresponding set of computer instructions that upon execution would cause an associated processor to perform the functionality described herein. Thus, the various aspects of the disclosure may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Another embodiment of the disclosure may provide a non-transitory machine and/or computer-readable storage and/or media, having stored thereon, a machine code and/or a computer program having at least one code section executable by a machine and/or a computer, thereby causing the machine and/or computer to perform the steps as described herein for generating a novel molecular structure using a protein structure.

The present disclosure may also be embedded in a computer program product, which comprises all the features enabling the implementation of the methods described herein, and which when loaded in a computer system is able to carry out these methods. Computer program in the present context means any expression, in any language, code or notation, either statically or dynamically defined, of a set of instructions intended to cause a system having an information processing capability to perform a particular function either directly or after either or both of the following: a) conversion to another language, code or notation; b) reproduction in a different material form.

Further, those of skill in the art will appreciate that the various illustrative logical blocks, modules, circuits, algorithms, and/or steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, sequences and/or algorithms described in connection with the embodiments disclosed herein may be embodied directly in firmware, hardware, in a software module executed by a processor, or in a combination thereof. A software module may reside in RAM memory, flash memory, ROM memory, EPROM memory, EEPROM memory, registers, hard disk, physical and/or virtual disk, a removable disk, a CD-ROM, virtualized system or device such as a virtual server or container, or any other form of storage medium known in the art. An exemplary storage medium is communicatively coupled to the processor (including logic/code executing in the processor) such that the processor can read information from, and write information to, the storage medium. In the alternative, the storage medium may be integral to the processor.

While the present disclosure has been described with reference to certain embodiments, it will be noted understood by, for example, those skilled in the art that various changes and modifications could be made and equivalents may be substituted without departing from the scope of the present disclosure as defined, for example, in the appended claims. In addition, many modifications may be made to adapt a particular situation or material to the teachings of the present disclosure without departing from its scope. The functions, steps and/or actions of the method claims in accordance with the embodiments of the disclosure described herein need not be performed in any particular order. Furthermore, although elements of the disclosure may be described or claimed in the singular, the plural is contemplated unless limitation to the singular is explicitly stated. Therefore, it is intended that the present disclosure is not limited to the particular embodiment disclosed, but that the present disclosure will include all embodiments falling within the scope of the appended claims.

What is claimed is:

1. A system, comprising:
a circuitry configured to:
receive, via one or more sources, a first input associated with a first scene, wherein the first input includes at least one of a plurality of images of a first user and a plurality of videos of the first user;
determine first context information associated with the first scene based on the received first input, wherein the first context information indicates circumstances, setting, and background information relating to a plurality of events within the first scene, and includes information about an emotional tone of the first scene and feelings and moods the first scene evokes;
extract a set of audio signals associated with a set of objects within the first scene based on the received first input, wherein the set of objects comprises of: animated objects, in-animated objects, or a combination thereof;
generate digital immersive content associated with the first scene based on the received first input, the determined first context information, and the extracted set of audio signals, wherein the generated digital immersive content comprises of at least a first virtual object of a set of virtual objects associated with the set of objects and a first audio signal of the extracted set of audio signals; and
render the generated digital immersive content via a user platform, wherein the user platform executes on a first user device associated with the first user.

2. The system according to claim 1, wherein the one or more sources comprises of the first user device.

3. The system according to claim 1, wherein at least one virtual object of the set of virtual objects is associated with the first user.

4. The system according to claim 1, wherein the first user is suffering from one or more psychological issues.

5. The system according to claim 1, wherein the digital immersive content assists in a treatment of one or more psychological issues associated with the first user.

6. The system according to claim 1, wherein the circuitry is further configured to:
identify a user platform to render the generated digital immersive content; and
render the digital immersive content via the identified user platform.

7. The system according to claim 1, wherein the user platform corresponds to a virtual reality (VR) application.

8. The system according to claim 1, wherein the user platform corresponds to one or more of: a web platform, a metaverse platform, an augmented reality (AR) application, a mobile application, a holographic application, or a wearable device application.

9. The system according to claim 1, wherein the first context information is indicative about a sensory feedback to be provided to the first user, and wherein the circuitry is further configured to:
control one or more sensors to provide the sensory feedback to the first user based on the determined first context information associated with the first scene, wherein the sensory feedback is provided while rendering the generated digital immersive content.

10. The system according to claim 9, wherein the one or more sensors are embedded within a suit worn by the first user.

11. The system according to claim 1, wherein the circuitry is further configured to:
determine weather conditions associated with the first scene based on the determined first context information;
generate a first virtual scene in a virtual environment based on the determined weather conditions associated with the first scene; and
render the first virtual scene in the virtual environment, as the digital immersive content, via the user platform.

12. The system according to claim 1, wherein the circuitry is further configured to:
translate the first audio signal from a first language to a second language based on one or more preferences of the first user; and
render the generated digital immersive content via the user platform, wherein the generated digital immersive content comprises of the translated first audio signal.

13. A method comprising:
receiving, via one or more sources, a first input associated with a first scene, wherein the first input includes at least one of a plurality of images of a first user and a plurality of videos of the first user;
determining first context information associated with the first scene based on the received first input, wherein the first context information indicates circumstances, setting, and background information relating to a plurality of events within the first scene, and includes information about an emotional tone of the first scene and feelings and moods the first scene evokes;
extracting a set of audio signals associated with a set of objects within the first scene based on the received first input, wherein the set of objects comprises of: animated objects, in-animated objects, or a combination thereof;
generating digital immersive content associated with the first scene based on the received first input, the determined first context information, and the extracted set of audio signals, wherein the generated digital immersive content comprises of at least a first virtual object of a set of virtual objects associated with the set of objects and a first audio signal of the extracted set of audio signals; and
rendering the generated digital immersive content via a user platform associated with the first user, wherein the user platform executes on a first user device associated with the first user.

14. The method according to claim 13, wherein the first virtual object of the set of virtual objects is associated with the first user.

15. The method according to claim 13, wherein the first user is suffering from one or more psychological issues, and wherein the digital immersive content assists in a treatment of one or more psychological issues associated with the first user.

16. The method according to claim 13, wherein the user platform corresponds to one or more of: a virtual reality (VR) application, a web platform, a metaverse platform, an augmented reality (AR) application, a mobile application, a holographic application, or a wearable device application.

17. The method according to claim 13, wherein the first context information is indicative about a sensory feedback to be provided to the first user, and wherein the method further comprising:
controlling one or more sensors, embedded within a suit worn by the first user, to provide the sensory feedback to the first user based on the determined first context information of the first scene, wherein the sensory feedback is provided while rendering the generated digital immersive content.

18. The method according to claim 13, further comprising:
determining weather conditions associated with the first scene based on the determined first context information;
generating a first virtual scene in a virtual environment based on the determined weather conditions associated with the first scene; and
rendering the first virtual scene in the virtual environment, as the digital immersive content, via the user platform.

19. The method according to claim 13, further comprising:
translating the first audio signal from a first language to a second language based on one or more preferences of the first user; and
rendering the generated digital immersive content via the user platform, wherein the generated digital immersive content comprises of the translated first audio signal.

20. A non-transitory computer-readable medium including computer program instructions, which when executed by a system, cause the system to perform one or more operations comprising:
receiving, via one or more sources, a first input associated with a first scene,
wherein the first input includes at least one of a plurality of images of a first user and a plurality of videos of the first user;
determining first context information associated with the first scene based on the received first input, wherein the first context information indicates circumstances, setting, and background information relating to a plurality of events within the first scene, and includes information about an emotional tone of the first scene and feelings and moods the first scene evokes;
extracting a set of audio signals associated with a set of objects within the first scene based on the received first input, wherein the set of objects comprises of: animated objects, in-animated objects, or a combination thereof;
generating digital immersive content associated with the first scene based on the received first input, the determined first context information, and the extracted set of audio signals, wherein the generated digital immersive content comprises of at least a first virtual object of a set of virtual objects associated with the set of objects and a first audio signal of the extracted set of audio signals; and rendering the generated digital immersive content via a user platform associated with the first user, wherein the user platform executes on a first user device associated with the first user.

\* \* \* \* \*